United States Patent
Arisoy et al.

(10) Patent No.: US 9,849,633 B2
(45) Date of Patent: Dec. 26, 2017

(54) REMOVING SHARP CUSPS FROM 3D SHAPES FOR ADDITIVE MANUFACTURING

(71) Applicant: Siemens Product Lifecycle Management Software Inc., Plano, TX (US)

(72) Inventors: Erhan Arisoy, Pittsburgh, PA (US); Suraj Ravi Musuvathy, Glenmont, NY (US); Livio Dalloro, Princeton, NJ (US)

(73) Assignee: Siemens Product Lifecycle Management Software Inc., Plano, TX (US)

( * ) Notice: Subject to any disclaimer, the term of this patent is extended or adjusted under 35 U.S.C. 154(b) by 649 days.

(21) Appl. No.: 14/311,990

(22) Filed: Jun. 23, 2014

(65) Prior Publication Data

US 2015/0367578 A1 Dec. 24, 2015

(51) Int. Cl.
| | |
|---|---|
| G06F 19/00 | (2011.01) |
| G06F 17/50 | (2006.01) |
| B29C 67/00 | (2017.01) |
| G06F 17/10 | (2006.01) |
| G05B 15/02 | (2006.01) |
| G06T 19/20 | (2011.01) |
| A61B 34/10 | (2016.01) |
| B29C 64/386 | (2017.01) |
| B33Y 50/02 | (2015.01) |

(52) U.S. Cl.
CPC .......... B29C 67/0088 (2013.01); A61B 34/10 (2016.02); B29C 64/386 (2017.08); G05B 15/02 (2013.01); G06F 17/10 (2013.01); G06F 17/50 (2013.01); G06T 19/20 (2013.01); A61B 2034/108 (2016.02); B33Y 50/02 (2014.12)

(58) Field of Classification Search
CPC ............ G06T 17/10; G06T 19/20; G06T 7/13
See application file for complete search history.

(56) References Cited

U.S. PATENT DOCUMENTS

| | | | | |
|---|---|---|---|---|
| 6,810,295 | B1 * | 10/2004 | Hochenauer | G06T 17/10 700/182 |
| 7,747,305 | B2 * | 6/2010 | Dean | A61F 2/30942 345/420 |
| 8,836,701 | B1 * | 9/2014 | Rockwood | G06F 17/50 345/419 |
| 9,026,407 | B1 * | 5/2015 | Kennefick | G06T 19/20 703/1 |
| 9,542,525 | B2 * | 1/2017 | Arisoy | G06F 17/5086 |

(Continued)

OTHER PUBLICATIONS

PCT Search Report dated Sep. 18, 2015 corresponding to PCT International Application PCT/US2015/035912 filed Jun. 16, 2015 (9 pages).

*Primary Examiner* — Michael D Masinick
*Assistant Examiner* — Derrick Boateng (57) ABSTRACT

A method for processing a three-dimensional (3D) mesh model includes receiving a 3D mesh model. One or more regions including a potential sharp cusp are automatically detected. The automatically detected one or more regions are displayed to a user and an active region of the 3D mesh model is defined by the user. Sphere fitting and Laplacian smoothing are applied to the designated active region to remove a sharp cusp therefrom and to obtain a modified 3D mesh model.

18 Claims, 4 Drawing Sheets

(56) References Cited

U.S. PATENT DOCUMENTS

| | | | |
|---|---|---|---|
| 2002/0164061 A1* | 11/2002 | Paik | G06T 7/0012 382/131 |
| 2004/0075659 A1 | 4/2004 | Taubin | |
| 2006/0094951 A1* | 5/2006 | Dean | A61F 2/30942 600/407 |
| 2008/0220395 A1* | 9/2008 | Marshall | A61C 13/0004 433/215 |
| 2008/0262814 A1* | 10/2008 | Zheng | G06F 19/3437 703/11 |
| 2009/0148816 A1* | 6/2009 | Marshall | A61C 13/0004 433/223 |
| 2010/0290679 A1 | 11/2010 | Gasser | |
| 2011/0058720 A1* | 3/2011 | Lu | G06T 7/12 382/131 |
| 2011/0202046 A1* | 8/2011 | Angeley | G06T 7/149 606/6 |
| 2012/0010711 A1* | 1/2012 | Antonyshyn | A61F 2/2875 623/16.11 |
| 2014/0341451 A1* | 11/2014 | Angeley | G06T 7/149 382/128 |
| 2014/0375636 A1* | 12/2014 | Young | G06F 17/50 345/420 |
| 2015/0178988 A1* | 6/2015 | Montserrat Mora | G06T 13/40 345/420 |
| 2015/0328004 A1* | 11/2015 | Mafhouz | G06F 17/50 700/98 |
| 2015/0367578 A1* | 12/2015 | Arisoy | B29C 67/0088 700/98 |
| 2015/0370958 A1* | 12/2015 | Arisoy | G06F 17/5086 700/98 |
| 2016/0157751 A1* | 6/2016 | Mahfouz | A61B 5/062 600/409 |
| 2017/0027756 A1* | 2/2017 | Angeley | G06T 7/149 |

* cited by examiner

REMOVING SHARP CUSPS FROM 3D SHAPES FOR ADDITIVE MANUFACTURING

TECHNICAL FIELD

The present disclosure relates to 3D shapes and, more specifically, to removing sharp cusps from 3D shapes for additive manufacturing.

DISCUSSION OF THE RELATED ART

Personalized medical devices are devices that have been custom-made to conform to the anatomy of a particular patient. Personalized medical devices may have a wide variety of uses and may be designed for use inside and outside the patient's body as tools, hardware, implants, prosthetics, etc.

This technology is presently used in and has great potential to be used in medical fields such as orthopedics, dentistry, cardiology, audiology, podiatry, surgery, etc.

One particular example of personalized medical devices includes replacement artificial bones and orthopedic implants. These devices must be custom-made according to the anatomy of the patient. This customization process may take considerable time and expense, which may be particularly problematic for patients who must wait for the device to be manufactured, often without the ability to function independently.

The growing availability of 3D printers has made on-site fabrication of personalized medical devices more readily accessible. The process for fabricating personalized medical devices often includes a technician manually editing a computer aided design (CAD) of a medical device to conform to the anatomy of a particular patient. After the CAD has been so edited, it may be sent to a 3D printer, which may be able to quickly create the device in accordance with the edited design, without having to wait what could otherwise be weeks.

SUMMARY

A method for processing a three-dimensional (3D) mesh model includes receiving a 3D mesh model. One or more regions including a potential sharp cusp are automatically detected. The automatically detected one or more regions are displayed to a user. Input designating an active region of the 3D mesh model is received from the user. Sphere fitting and Laplacian smoothing are applied to the designated active region to remove a sharp cusp therefrom and to obtain a modified 3D mesh model.

The received 3D mesh model may include image data obtained from a medical imaging device. The medical imaging device may be a computed tomography (CT) scanner.

Automatically detecting the one or more regions including a potential sharp cusp may include checking a deviation of face normals between neighboring normal and determining whether this deviation exceeds a predetermined threshold.

Automatically detecting the one or more regions including a potential sharp cusp may include selecting a seed point close to a potential sharp cusp, growing a region around the selected seed point, checking a deviation of face normals between neighboring normal within the growing region, and terminating the region growing when the deviation exceeds a predetermined threshold. The seed point may be provided by the user.

The user may designate the active region of the 3D mesh model by selecting from among the displayed automatically detected one or more regions including a potential sharp cusp.

In applying sphere fitting and Laplacian smoothing to the designated active region, a degree of sphere fitting-based inflation and a degree of surface area minimizing Laplacian forces may be used to determine an extent of the sphere fitting and Laplacean smoothing, respectively. The user may be provided with a display of the modified 3D mesh model. The user may be provided with an opportunity to modify one or both of the degree of sphere fitting-based inflation and the degree of surface area minimizing Laplacian forces.

Applying sphere fitting and Laplacian smoothing may include performing Laplacian energy minimization in an iterative fashion.

A custom medical device may be manufactured from the modified 3D mesh model using a 3D printer.

A method for manufacturing a personalized medical device includes acquiring an image including a patient anatomical geometry. A three-dimensional (3D) mesh model is created from the acquired image. One or more regions including a potential sharp cusp are automatically detected from the created 3D mesh model. An active region is designated from among the one or more automatically detected regions. Sphere fitting and Laplacian smoothing are applied to the designated active region to remove a sharp cusp therefrom and to obtain a modified 3D mesh model. The modified 3D mesh model is 3D printed using a 3D printer.

Designating an active region from among the one or more automatically detected region may include displaying the automatically detecting one or more regions to a user and receiving input, from the user, designating an active region of the 3D mesh model.

The user may designate the active region of the 3D mesh model by selecting from among the displayed automatically detected one or more regions including a potential sharp cusp.

The image including the patient anatomical geometry may be acquired using a computed tomography (CT) scanner.

Automatically detecting the one or more regions including a potential sharp cusp may include checking a deviation of face normals between neighboring normal and determining whether this deviation exceeds a predetermined threshold.

Automatically detecting the one or more regions including a potential sharp cusp may include selecting a seed point close to a potential sharp cusp, growing a region around the selected seed point, checking a deviation of face normals between neighboring normal within the growing region, and terminating the region growing when the deviation exceeds a predetermined threshold.

The seed point may be provided by the user.

In applying sphere fitting and Laplacian smoothing to the designated active region, a degree of sphere fitting-based inflation and a degree of surface area minimizing Laplacian forces may be used to determine an extent of the sphere fitting and Laplacian smoothing, respectively. The user may be provided with a display of the modified 3D mesh model. The user may be provided with an opportunity to modify one or both of the degree of sphere fitting-based inflation and the degree of surface area minimizing Laplacian forces.

Applying sphere fitting and Laplacian smoothing may include performing Laplacian energy minimization in an iterative fashion.

A computer system includes a processor and a non-transitory, tangible, program storage medium, readable by the computer system, embodying a program of instructions executable by the processor to perform method steps for processing a three-dimensional (3D) mesh model. The method includes receiving a 3D mesh model, automatically detecting one or more regions including a potential sharp cusp, displaying the automatically detecting one or more regions to a user and receiving input, from the user, designating an active region of the 3D mesh model, and applying sphere fitting and Laplacian smoothing to the designated active region to remove a sharp cusp therefrom and to obtain a modified 3D mesh model.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiment of the present invention seek to provide systems and methods for designing and manufacturing personalized medical devices. These personalized medical devices may be fabricated from CAD models, which may be 3D polygonal mesh models. A template model may be modified in accordance with the exact anatomical geometry of a patient and this modified model may then be fabricated using a 3D printer.

The anatomical geometry of a patient may be acquired using a medical imaging device such as a computed tomography (CT) scanner, magnetic resonance imager (MRI), or from multiple 2D images acquired from different angles using a C-arm mounted x-ray device. As personalized medical devices may also be placed outside of the patient's body, for example, as a cast for setting a broken arm, imaging devices such as stereoscopic digital camera, 3D laser scanners, or the like may be used acquire 3D patient geometry. The anatomical geometry may thereafter be incorporated into a designed CAD model for the medical device being constructed.

However, geometric operations that may be used in the design of the personalized medical devices, such as offsets, non-uniform scaling, and non-rigid deformations, may result in one or more sharp cusps in the objects. These cusps may look like deep valleys. These sharp cusps may be undesirable as they can cause stress points during manufacturing as well as deployment leading to breakages and product failures. For example, where a personalized medical device is a replacement bone, a sharp cusp in the model may lead to the production of a device that has a weak point where the device may be susceptible to breakage.

In order to mitigate such problems, exemplary embodiments of the present invention provide an interactive method to increase the quality of such models by detecting regions of sharp cusps, facilitate intelligent interactive editing of the detected sharp cusp regions and inflate the regions to remove the sharp cusps, all while preserving important geometric features and refraining from modifying sharp regions that are intended to be sharp.

The detection and treatment of these sharp cusps may involve mesh fairing. A first group of suitable mesh fairing techniques may be based on geometric flows. Here, mesh smoothing problem are defined as an energy minimization problem such as curvature, gradient, surface area or volume. According to one such approach, Laplacian based smoothing algorithm may be used for mesh fairing. In its simplest formulation, Laplacian smoothing repositions vertices of the original mesh to the barycenter of their one-ring neighbors. Here, the integral of the sum of the maximal and minimal principal curvatures may be used to perform energy minimization. According to other approaches, a spring model may be used to minimize variation of curvature energy for generation of blobby looking geometries. Although these methods may be powerful tools for mesh fairing, these solutions might result in too much energy loss and loss of fine details on the original geometry such as sharp edges or high curvature regions. In order to mitigate this drawback, an anisotropic discrete filter formulation based on local principal curvature values may be used to detect local sharp regions. A smoothing algorithm based on the detection results may apply different amount of minimization locally. However, this decision may be based on previously defined thresholds and might result in loss of local features. Other similar mesh fairing techniques may involve mean curvature flow based smoothing.

A second group of suitable mesh fairing techniques may make use of spectral methods that may adapt techniques from the image processing domain. Moreover, bilateral filters may be applied to discrete surfaces to denoise surfaces while preserving sharp features. Eigenvectors of meshes with number of vertices greater than a couple of thousands may also be efficiently calculated. Techniques for doing this may be based on calculating a Fourier like transformation on meshes using Manifold Harmonic Basis functions and then applying a band pass filtering on this transformation.

A third group of suitable mesh fairing techniques may involve optimization based techniques which provide a certain smoothness quality while minimizing different energy functions. For example, Laplacian smoothing may be combined with optimization to increase mesh quality. For example, Laplacian Mesh optimization based on least square meshes may be used. Here, smoothing is not applied iteratively; instead it is calculated in one step by solving a linear system of equations. This formulation not only preserves Laplacian coordinates but also puts some positional soft constraints in order to preserve local features.

Although each of these three groups differ based on their formulations, they all try to achieve mesh fairing based on repositioning of the vertices on the original object. These methods do not remesh or change the mesh topology of the input geometry. Among all these repositioning methodologies, optimal Delaunay Triangulation may be particularly effective in terms of mesh smoothing for 2D meshes, but extending this idea to 3D is not trivial and computationally costly. A Delaunay triangulation method may be used to increase mesh quality by extending original ODT to surface meshes. Such a formulation aims to minimize a quadratic optimization problem where the solution not only increases the quality of the underlying mesh structure but also remove noise while respecting local properties.

One-shot solutions such as optimization based mesh smoothing algorithms or spectral techniques may be especially suitable for the removal of noise that exists on the entire geometric object without deteriorating local features such as sharp creases or corners. Alternatively, Laplacian or curvature minimization based fairing tools may be used. These techniques may be tailored towards beatification of existing triangle qualities locally or globally in an iterative fashion that enables high user control during the smoothing process. However, most of these approaches require mesh distribution on the original model to be well aligned with the sharp cusp. For such cases, operations similar to beveling may be used to convert sharp cusps to smooth transitions without changing topology of the underlying model. However, especially in the generation of patient specific medical devices, the sharp cusps may usually be a result of the inflation or scaling operations performed in intermediate steps that might result in low quality mesh alignments with the sharp cusps.

Exemplary embodiments of the present invention may accordingly utilize techniques for cusp removal that are computationally light to provide interactive feedback and provide local control for the user. In order to remove problematic self intersections or cusps, these vertex positions may first be regularized and then inflated while preserving local properties. One contribution of exemplary embodiments of the present invention is the development of a cusp detection and removal technique that is based on sphere fitting and Laplacian smoothing which minimizes surface area and local variation of curvature on the input geometry through user interactions.

Figure 1:
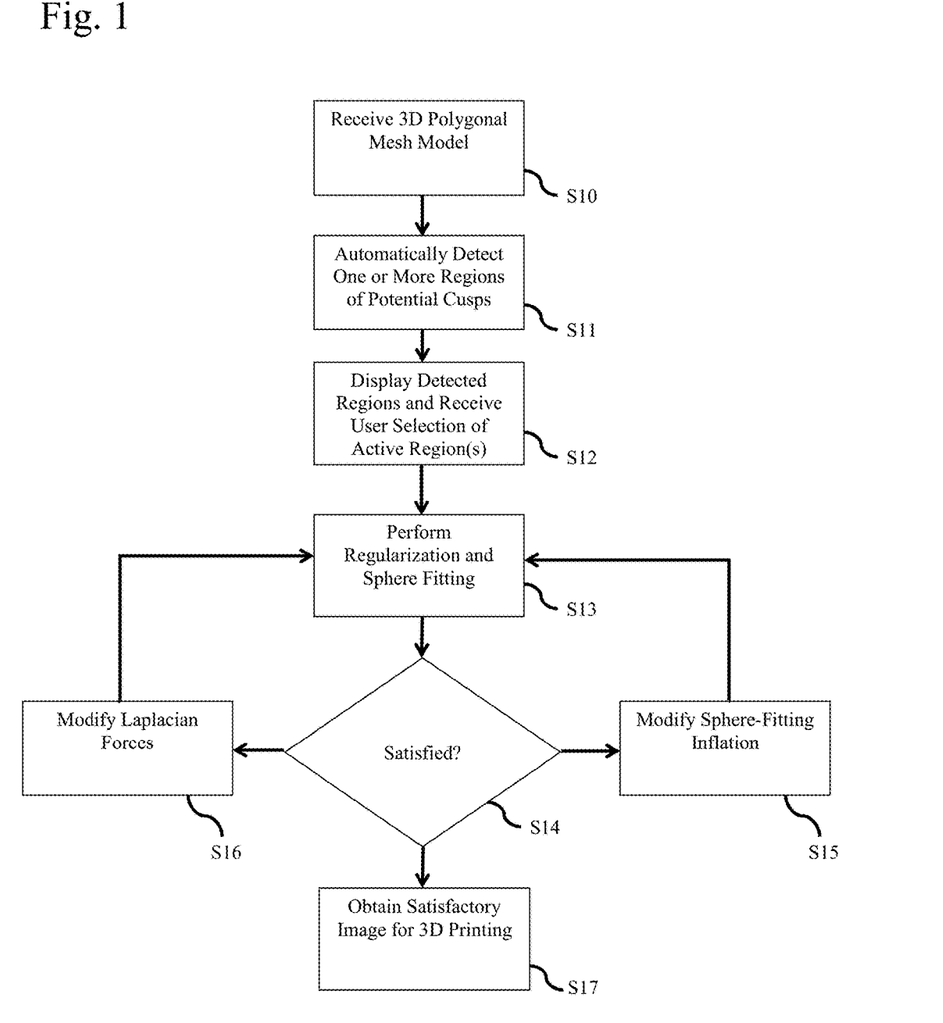
FIG. 1 is a flow chart illustrating an approach for manufacturing custom medical devices in accordance with exemplary embodiments of the present invention.

FIG. 1 is a flow chart illustrating an approach for manufacturing custom medical devices in accordance with exemplary embodiments of the present invention. Although the disclosure describes exemplary embodiments of the present invention in these terms, it is to be understood that the present invention may be applied more generally to the removal of sharp cusps from 3D models, and accordingly, it should be appreciated that the manufacturing of custom medical devices is an example of one particular application of the instant invention.

First, a 3D polygonal mesh representing, at least in part, an organic form is received (Step S10). The 3D polygon mesh may have been acquired, or otherwise based on an image that was acquired, from a medical imaging scan such as a computed tomography (CT) scan of a patient's anatomy. The 3D polygonal mesh may represent a design for a custom medical device. Automatic region detection may then be performed to detect one or more regions including sharp cusps in the initial geometry (Step S11). These possible cusps may be problematic in subsequent manufacturing steps because of unexpected stress point generations.

Automatic region detection may takes a seed point as input and then grows this region on the surface of the 3D model. Potential cusps may be identified by checking the deviation of face normals between neighboring normals. Region growing may be terminated when the deviation is larger then a predetermined threshold. For example, this parameter may be set to an angle of 50 degrees. Here, potential cusps may be identified as either a global sharp edge, which may be expected, or a local cusp, which may be corrected. For example, sharp edges of the type typically arising from designed CAD geometries need not be considered. In order to differentiate these two cases, it may be checked whether this normal change is consistent with the average normal of the local neighborhood. Exemplary embodiments of the present invention may highlight regions with high cusp probabilities and then enable the user to label a region on the 3D polygonal mesh as active in the subsequent step. The active region may be a portion of the model that is currently being edited. Where multiple regions of a model are to be edited, these regions may be edited one-by-one with the portion currently being edited referred to herein as the "active" region.

After the identification of such problematic regions, a visual feedback may then be provided to the user to display the automatically detected sharp cusp regions. In this display, problematic triangles involved in the generation of a cusp or triangles that are in the close neighborhood of them may be highlighted. The display may prompt a user to select a region of interest on the original model and the user's input may be received (Step S12). The user input may include a manual selection of one or more regions of interest that may include sharp cusps. The user may select from among the automatically highlighted regions but the user may also be free to select another region. The user input may be in the form of a highlighting/painting of a region or a touch/click within a region highlighted as part of the prior step. In either case, subsequent sharp cusp removal may be limited to sharp cusps located within the identified region(s) of interest, and in this way, the user may see that sharp cusps are not removed from regions that are intended to have sharp edges. The user's selection may therefore constitute a local shape preserving region.

After the user has finished labeling, exemplary embodiments of the present invention may check whether the region the user painted as active includes any sharp edges based on the local normal deviations. Sharp cusps located within the regions labeled by the user as active may be processed while sharp cusps not located within the labeled region may be left unmodified.

Figure 2:
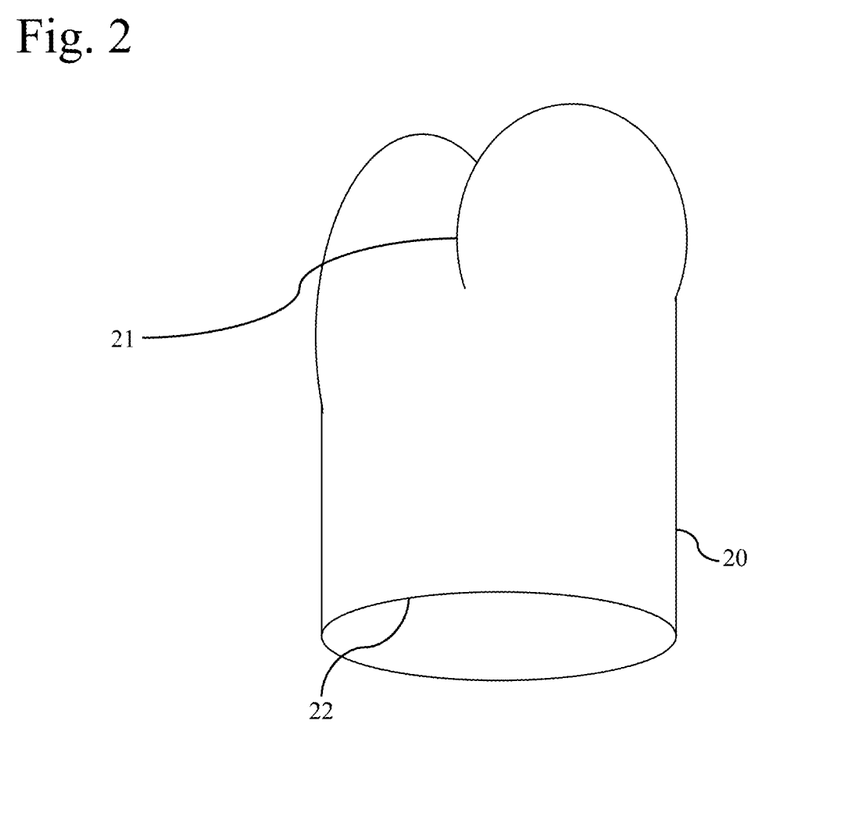
FIG. 2 is a schematic illustration distinguishing between a cusp region, which may require remediation, and a sharp edge, which may be an acceptable feature of the shape model in accordance with exemplary embodiments of the present invention.

FIG. 2 is a schematic illustration distinguishing between a cusp region, which may require remediation, and a sharp edge, which may be an acceptable feature of the shape model. As can be seen from this figure, the shape model 20 includes a cusp region 21. The cusp region is a sharp crease in the 3D surface of the shape model 20. The local sharp edge 21 is merely a side of the shape model 20 and thus requires no correction.

Figure 3:
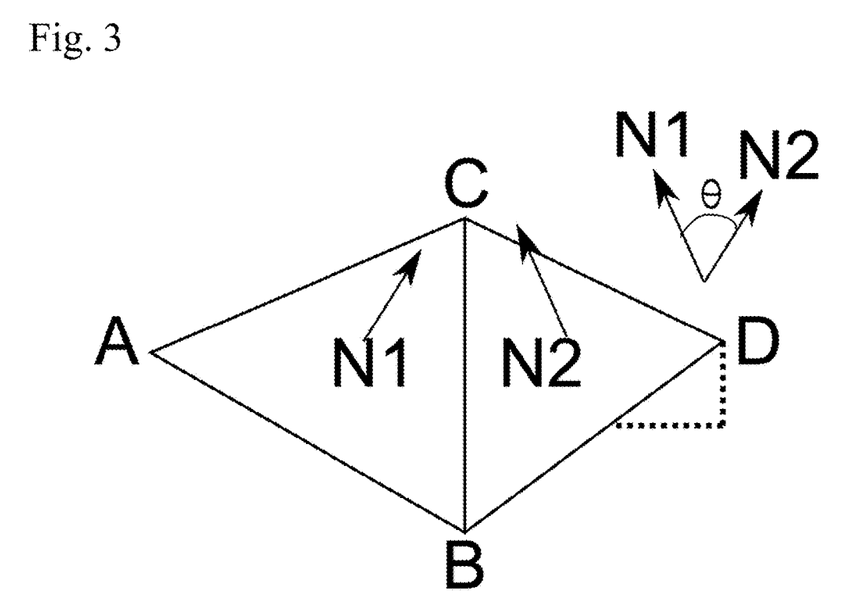
FIG. 3 is a diagram illustrating an approach for automatically identifying a sharp cusp region in accordance with exemplary embodiments of the present invention.

FIG. 3 is a diagram illustrating an approach for automatically identifying a sharp cusp region in accordance with exemplary embodiments of the present invention. As discussed above, an angle θ between two neighboring triangles N1 (formed by points A, B, and C) and N2 (formed by points B, C, and D) may be used to identify cusps, for example, where θ exceeds a predetermined angle.

Cusps may thereafter be automatically removed from within the active region of interest in an iterative fashion. This may be performed by regularization and sphere fitting (Step S13). In performing regularization and sphere fitting, two main weights may be used to control the magnitude of the cusp removal technique applied during this process. These weights may include a measure of sphere fitting-based inflation and a measure of surface area minimizing Laplacian forces, as described in greater detail below. The user may be provided with the opportunity to modify one of both of these factors to obtain a desired degree of cusp removal (Step S14). For example, the user may modify sphere-fitting inflation (Step S15) and then see the results of the modification to determine if the user is satisfied with these new results. The user may alternatively, or additionally, modify Laplacian forces (S16) and then see the results of the modification to determine if the user is satisfied with these new results.

Exemplary embodiments of the present invention may therefore provide for the automatic detection of such defective regions and the removal of sharp creases while preserving local smoothness without causing self-intersections.

Sphere fitting based smoothing may be performed with the Laplacian energy minimization in an iterative fashion. This operation may be construed as a combination of minimization of variation of curvature information with the area energy. In order to inflate vertices while uniformly regularizing the vertices, exemplary embodiments of the present invention may assume that the vertices on the final surface will all lie on local spheres with respect to each other.

It may be assumed that in the final surface all points will lie approximately on a sphere fitted to the local neighborhood of each vertex. Based on this assumption, on the final surface each vertex position may be held to satisfy the following three equations:

$$P_{xi} = C_{xlocalsphere} + r*N_{xi}$$

$$P_{yi} = C_{ylocalsphere} + r*N_{yi}$$

$$P_{zi} = C_{zlocalsphere} + r*N_{zi} \quad (1)$$

where C is the center of the sphere with radius r, N is the vertex normal and P is the vertex position.

The local sphere fitting problem may then be solved by calculating the center and radius of the local sphere in a linear least square fashion. The three equations (1) may be expressed for every vertex in the one ring neighborhood of each vertex and a sphere center and radius may be assigned to these vertices. The following matrix describes a linear least square system that may be used in accordance with exemplary embodiments of the present invention, where A is a matrix of size 3n×4, X is a matrix if size 4×1 and B is a matrix of size 3n×1. Here n may be a number of neighbors in one ring neighborhood.

$$\underbrace{\begin{pmatrix} 1 & 0 & 0 & N_{x1} \\ 0 & 1 & 0 & N_{y1} \\ 0 & 0 & 1 & N_{z1} \\ \vdots & \vdots & \ddots & \vdots \\ 0 & 0 & 1 & N_{zn} \end{pmatrix}}_{A} \underbrace{\begin{pmatrix} Center_x \\ Center_y \\ Center_z \\ radius \end{pmatrix}}_{X} = \underbrace{\begin{pmatrix} P_{x1} \\ P_{y1} \\ P_{z1} \\ \vdots \\ P_{zn} \end{pmatrix}}_{B} \quad (2)$$

To solve this linear least square system, exemplary embodiments of the present invention may use normal equations $(A^tA)X=A^tB$ and a desired solution may be given by $X=(A^tA)-1A^tB$. After finding the center and radius of the local sphere, exemplary embodiments of the present invention may calculate an inflation force based on the projection of each vertex on this local sphere. The following equations may be used for projection and inflation force calculations. Here the factor μ affects the amount of inflation for each vertex. According to some exemplary embodiments of the present invention, an inflation of 2 percent may be used to obtain satisfactory results. The user may be permitted to adjust this parameter to increase the amount of inflation, where desired:

$$v_i^{n+1} = w_{originalposition}*v_i^n + w_{sphere}*(Center+(radius+\mu)*N_i) \quad (3)$$

$$\text{Inflation}(v_i) = (v_i^{n+1} - v_i^n) \quad (4)$$

The overall cusp removal tool may be a combination of the sphere fitting based inflation forces with the surface area minimizing Laplacian forces. These two weights may be used to balance the amount of forces acting on each vertex. The first one of these weights is the $W_{laplacian}$ which controls the effect of surface minimization in the cusp removal. If the user observes the removal tool results in low quality polygons, this factor can be manually increased in order to boost smoothing force or vice versa. The second weight $W_{inflation}$ controls the amount of inflation to remove and expand existing cusps. Exemplary embodiments of the present invention may keep this force low as large inflation displacements may tend to deteriorate the smoothness of the underlying 3D polygonal. The following equations may be utilized to calculate Laplacian forces and final cusp removal force:

$$Laplace(v_i) = \sum_{j=0}^{n} \frac{1}{(\|v_j - v_i\|)} * (v_i - v_j) \quad (5)$$

$$Fcuspremove(v_i) = w_{laplacian} * Laplace(v_i) + w_{inflation} * \text{Inflation}(v_i) \quad (6)$$

Exemplary embodiments of the present invention may utilize the above-described cusp removal tool on a rich number of cases and significant initial mesh quality may be obtained. This cusp removal tool may be utilized in wide variety of applications where post mesh processing operations are necessary to generate cusp free models suitable for 3D printing.

Accordingly, after cusp removal has been performed utilizing inflation and sphere fitting to the satisfaction of the user (Yes, Step S14), a cusp-removed 3D polygon mesh model may be obtained (Step S17) for use in 3D printing.

Administration of the above steps may be performed with the use of a computer system, as described in detail below.

Figure 4:
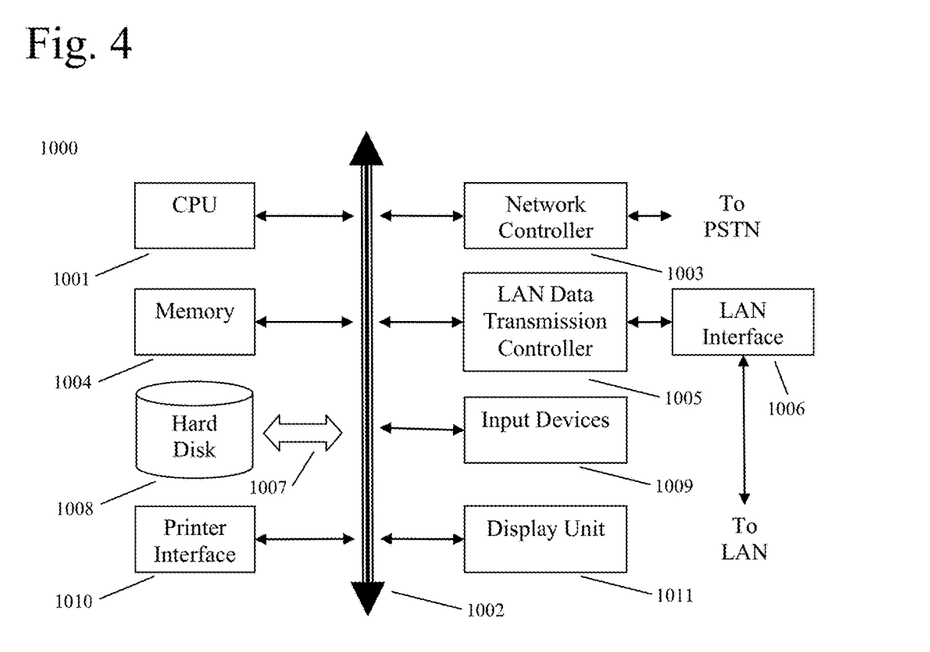
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for processing a three-dimensional (3D) mesh model, comprising:
receiving a 3D mesh model;
automatically detecting one or more regions including a potential sharp cusp;
displaying the automatically detected one or more regions to a user and receiving input, from the user, designating an active region of the 3D mesh model; and
applying sphere fitting and Laplacian smoothing to the designated active region to remove a sharp cusp therefrom and to obtain a modified 3D mesh model, wherein applying the sphere fitting and Laplacian smoothing includes performing Laplacian energy minimization in an iterative fashion.

2. The method of claim 1, wherein the received 3D mesh model includes image data obtained from a medical imaging device.

3. The method of claim 2, wherein the medical imaging device is a computed tomography (CT) scanner.

4. The method of claim 1, wherein automatically detecting the one or more regions including a potential sharp cusp, comprises checking a deviation of face normals between neighboring normal and determining whether this deviation exceeds a predetermined threshold.

5. The method of claim 1, wherein automatically detecting the one or more regions including a potential sharp cusp, comprises:
selecting a seed point close to a potential sharp cusp;
growing a region around the selected seed point;
checking a deviation of face normals between neighboring normal within the growing region; and
terminating the region growing when the deviation exceeds a predetermined threshold.

6. The method of claim 5, wherein the seed point is provided by the user.

7. The method of claim 1, wherein the user designates the active region of the 3D mesh model by selecting from among the displayed automatically detected one or more regions including a potential sharp cusp.

8. The method of claim 1, wherein in applying sphere fitting and Laplacian smoothing to the designated active region:
a degree of sphere fitting-based inflation and a degree of surface area minimizing Laplacian forces are used to determine an extent of the sphere fitting and Laplacean smoothing, respectively;
the user is provided with a display of the modified 3D mesh model; and
the user is provided with an opportunity to modify one or both of the degree of sphere fitting-based inflation and the degree of surface area minimizing Laplacian forces.

9. The method of claim 1, additionally comprising manufacturing a custom medical device from the modified 3D mesh model using a 3D printer.

10. A method for manufacturing a personalized medical device, comprising:
acquiring an image including a patient anatomical geometry;
creating a three-dimensional (3D) mesh model from the acquired image;
automatically detecting one or more regions including a potential sharp cusp from the created 3D mesh model;
designating an active region from among the one or more automatically detected regions;
applying sphere fitting and Laplacian smoothing to the designated active region to remove a sharp cusp therefrom and to obtain a modified 3D mesh mode wherein applying the sphere fitting and Laplacian smoothing includes performing Laplacian energy minimization in an iterative fashion; and
3D printing the modified 3D mesh model using a 3D printer.

11. The method of claim 1, wherein designating an active region from among the one or more automatically detected region, comprises:
displaying the automatically detecting one or more regions to a user; and
receiving input, from the user, designating an active region of the 3D mesh model.

12. The method of claim 11, wherein the user designates the active region of the 3D mesh model by selecting from among the displayed automatically detected one or more regions including a potential sharp cusp.

13. The method of claim 10, wherein the image including the patient anatomical geometry is acquired using a computed tomography (CT) scanner.

14. The method of claim 10, wherein automatically detecting the one or more regions including a potential sharp cusp, comprises checking a deviation of face normals between neighboring normal and determining whether this deviation exceeds a predetermined threshold.

15. The method of claim 10, wherein automatically detecting the one or more regions including a potential sharp cusp, comprises:
selecting a seed point close to a potential sharp cusp;
growing a region around the selected seed point;
checking a deviation of face normals between neighboring normal within the growing region; and
terminating the region growing when the deviation exceeds a predetermined threshold.

16. The method of claim 15, wherein the seed point is provided by the user.

17. The method of claim 10, wherein in applying sphere fitting and Laplacian smoothing to the designated active region:
a degree of sphere fitting-based inflation and a degree of surface area minimizing Laplacian forces are used to determine an extent of the sphere fitting and Laplacean smoothing, respectively;
the user is provided with a display of the modified 3D mesh model; and
the user is provided with an opportunity to modify one or both of the degree of sphere fitting-based inflation and the degree of surface area minimizing Laplacian forces.

18. A computer system comprising:
a processor; and
a non-transitory, tangible, program storage medium, readable by the computer system, embodying a program of instructions executable by the processor to perform method steps for processing a three-dimensional (3D) mesh model, the method comprising:
receiving a 3D mesh model;
automatically detecting one or more regions including a potential sharp cusp;

displaying the automatically detecting one or more regions to a user and receiving input, from the user, designating an active region of the 3D mesh model; and
applying sphere fitting and Laplacian smoothing to the designated active region to remove a sharp cusp therefrom and to obtain a modified 3D mesh model, wherein the Laplacian smoothing with Laplacian energy minimization in an iterative fashion.

* * * * *